(12) United States Patent
Komp et al.

(10) Patent No.: US 12,016,737 B2
(45) Date of Patent: Jun. 25, 2024

(54) SYSTEMS AND METHODS FOR DISPLAYING MEDICAL VIDEO IMAGES AND/OR MEDICAL 3D MODELS

(71) Applicant: Covidien LP, Mansfield, MA (US)

(72) Inventors: John W. Komp, Dillon, CO (US); Irena Cantrall, Boulder, CO (US); Francesca Rossetto, Longmont, CO (US); Robert W. Pierce, Franklin, MA (US); Fiona A. Morrison, Perth (GB); Mark N. Florio, Hamden, CT (US)

(73) Assignee: Covidien LP, Mansfield, MA (US)

( * ) Notice: Subject to any disclaimer, the term of this patent is extended or adjusted under 35 U.S.C. 154(b) by 225 days.

(21) Appl. No.: 17/592,270

(22) Filed: Feb. 3, 2022

(65) Prior Publication Data
US 2022/0163785 A1 May 26, 2022

Related U.S. Application Data

(63) Continuation of application No. 16/892,598, filed on Jun. 4, 2020, now Pat. No. 11,269,173.
(Continued)

(51) Int. Cl.
*G16H 30/20* (2018.01)
*A61B 1/00* (2006.01)
(Continued)

(52) U.S. Cl.
CPC ...... *A61B 90/361* (2016.02); *A61B 1/000094* (2022.02); *A61B 1/00055* (2013.01);
(Continued)

(58) Field of Classification Search
None
See application file for complete search history.

(56) References Cited

U.S. PATENT DOCUMENTS

| 8,335,359 B2 | 12/2012 | Fidrich et al. |
| 8,706,184 B2 | 4/2014 | Mohr et al. |

(Continued)

FOREIGN PATENT DOCUMENTS

| BR | 0013237 A | 7/2003 |
| BR | 0116004 A | 6/2004 |

(Continued)

OTHER PUBLICATIONS

Partial European Search Report issued in European Application No. 20191559.2 dated Feb. 1, 2021, 15 pages.
(Continued)

*Primary Examiner* — Eileen M Adams
(74) *Attorney, Agent, or Firm* — Weber Rosselli & Cannon LLP

(57) ABSTRACT

Computer-assisted surgical systems and methods provide intraoperative playback of and interaction with recorded video images and/or a 3D model while displaying current video images. The methods and related surgical systems involve capturing, by a two-dimensional (2D) or three-dimensional (3D) video camera, current video images and recording the captured video images. A user interface displays the current video images and the recorded video images and/or the 3D model and enables a user to interact with either or both of them.

18 Claims, 13 Drawing Sheets

Related U.S. Application Data

(60) Provisional application No. 62/888,892, filed on Aug. 19, 2019.

(51) Int. Cl.
  *A61B 1/05* (2006.01)
  *A61B 90/00* (2016.01)
  *G02B 23/24* (2006.01)

(52) U.S. Cl.
  CPC ............ *A61B 1/00194* (2022.02); *A61B 1/05* (2013.01); *G02B 23/2415* (2013.01); *G16H 30/20* (2018.01)

(56) References Cited

U.S. PATENT DOCUMENTS

| | | | |
|---|---|---|---|
| 8,827,934 | B2 | 9/2014 | Chopra et al. |
| 9,918,659 | B2 | 3/2018 | Chopra et al. |
| 10,373,719 | B2 | 8/2019 | Soper et al. |
| 10,376,178 | B2 | 8/2019 | Chopra |
| 10,405,753 | B2 | 9/2019 | Sorger |
| 10,478,162 | B2 | 11/2019 | Barbagli et al. |
| 10,480,926 | B2 | 11/2019 | Froggatt et al. |
| 10,524,866 | B2 | 1/2020 | Srinivasan et al. |
| 10,555,788 | B2 | 2/2020 | Panescu et al. |
| 10,610,306 | B2 | 4/2020 | Chopra |
| 10,638,953 | B2 | 5/2020 | Duindam et al. |
| 10,674,970 | B2 | 6/2020 | Averbuch et al. |
| 10,682,070 | B2 | 6/2020 | Duindam |
| 10,706,543 | B2 | 7/2020 | Donhowe et al. |
| 10,709,506 | B2 | 7/2020 | Coste-Maniere et al. |
| 10,772,485 | B2 | 9/2020 | Schlesinger et al. |
| 10,796,432 | B2 | 10/2020 | Mintz et al. |
| 10,823,627 | B2 | 11/2020 | Sanborn et al. |
| 10,827,913 | B2 | 11/2020 | Ummalaneni et al. |
| 10,835,153 | B2 | 11/2020 | Rafii-Tari et al. |
| 10,885,630 | B2 | 1/2021 | Li et al. |
| 2003/0013972 | A1 | 1/2003 | Makin |
| 2007/0080685 | A1* | 4/2007 | Bydder .............. G01R 33/4816 324/309 |
| 2007/0238981 | A1* | 10/2007 | Zhu ........................ A61B 34/20 600/424 |
| 2008/0071141 | A1 | 3/2008 | Gattani et al. |
| 2010/0249506 | A1 | 9/2010 | Prisco et al. |
| 2010/0281375 | A1* | 11/2010 | Pendergast ........... G11B 27/036 715/723 |
| 2013/0303945 | A1 | 11/2013 | Blumenkranz et al. |
| 2014/0035798 | A1 | 2/2014 | Kawada et al. |
| 2015/0123993 | A1* | 5/2015 | Ohba ........................ G09G 5/36 345/629 |
| 2015/0148690 | A1 | 5/2015 | Chopra et al. |
| 2015/0265368 | A1 | 9/2015 | Chopra et al. |
| 2016/0157939 | A1 | 6/2016 | Larkin et al. |
| 2016/0183841 | A1 | 6/2016 | Duindam et al. |
| 2016/0192860 | A1 | 7/2016 | Allenby et al. |
| 2016/0287344 | A1 | 10/2016 | Donhowe et al. |
| 2017/0079600 | A1 | 3/2017 | Bracken et al. |
| 2017/0112576 | A1 | 4/2017 | Coste-Maniere et al. |
| 2017/0209071 | A1 | 7/2017 | Zhao et al. |
| 2017/0245940 | A1 | 8/2017 | Piron et al. |
| 2017/0265952 | A1 | 9/2017 | Donhowe et al. |
| 2017/0311844 | A1 | 11/2017 | Zhao et al. |
| 2017/0319165 | A1 | 11/2017 | Averbuch |
| 2018/0078318 | A1 | 3/2018 | Barbagli et al. |
| 2018/0153621 | A1 | 6/2018 | Duindam et al. |
| 2018/0153632 | A1 | 6/2018 | Tokarchuk et al. |
| 2018/0235709 | A1 | 8/2018 | Donhowe et al. |
| 2018/0240237 | A1 | 8/2018 | Donhowe et al. |
| 2018/0256262 | A1 | 9/2018 | Duindam et al. |
| 2018/0263706 | A1 | 9/2018 | Averbuch |
| 2018/0279852 | A1 | 10/2018 | Rafii-Tari et al. |
| 2018/0325419 | A1 | 11/2018 | Zhao et al. |
| 2019/0000559 | A1 | 1/2019 | Berman et al. |
| 2019/0000560 | A1 | 1/2019 | Berman et al. |
| 2019/0008413 | A1 | 1/2019 | Duindam et al. |
| 2019/0015163 | A1 | 1/2019 | Abhari et al. |
| 2019/0038365 | A1 | 2/2019 | Soper et al. |
| 2019/0065209 | A1 | 2/2019 | Mishra et al. |
| 2019/0069957 | A1 | 3/2019 | Barral et al. |
| 2019/0110839 | A1 | 4/2019 | Rafii-Tari et al. |
| 2019/0110855 | A1 | 4/2019 | Barral et al. |
| 2019/0117379 | A1* | 4/2019 | Quirós ..................... A61F 2/12 |
| 2019/0175062 | A1 | 6/2019 | Rafii-Tari et al. |
| 2019/0183318 | A1 | 6/2019 | Froggatt et al. |
| 2019/0183585 | A1 | 6/2019 | Rafii-Tari et al. |
| 2019/0183587 | A1 | 6/2019 | Rafii-Tari et al. |
| 2019/0192234 | A1 | 6/2019 | Gadda et al. |
| 2019/0209016 | A1 | 7/2019 | Terzlinger et al. |
| 2019/0209043 | A1 | 7/2019 | Zhao et al. |
| 2019/0216548 | A1 | 7/2019 | Ummalaneni |
| 2019/0239723 | A1 | 8/2019 | Duindam et al. |
| 2019/0239831 | A1 | 8/2019 | Chopra |
| 2019/0250050 | A1 | 8/2019 | Sanborn et al. |
| 2019/0254649 | A1 | 8/2019 | Walters et al. |
| 2019/0269470 | A1 | 9/2019 | Barbagli et al. |
| 2019/0272634 | A1 | 9/2019 | Li et al. |
| 2019/0298160 | A1 | 10/2019 | Ummalaneni et al. |
| 2019/0298451 | A1 | 10/2019 | Wong et al. |
| 2019/0320878 | A1 | 10/2019 | Duindam et al. |
| 2019/0320937 | A1 | 10/2019 | Duindam et al. |
| 2019/0336238 | A1 | 11/2019 | Yu et al. |
| 2019/0343424 | A1 | 11/2019 | Blumenkranz et al. |
| 2019/0350659 | A1 | 11/2019 | Wang et al. |
| 2019/0365199 | A1 | 12/2019 | Zhao et al. |
| 2019/0365479 | A1 | 12/2019 | Rafii-Tari |
| 2019/0365486 | A1 | 12/2019 | Srinivasan et al. |
| 2019/0380787 | A1 | 12/2019 | Ye et al. |
| 2020/0000319 | A1 | 1/2020 | Saadat et al. |
| 2020/0000526 | A1 | 1/2020 | Zhao |
| 2020/0008655 | A1 | 1/2020 | Schlesinger et al. |
| 2020/0030044 | A1 | 1/2020 | Wang et al. |
| 2020/0030461 | A1 | 1/2020 | Sorger |
| 2020/0038750 | A1 | 2/2020 | Kojima |
| 2020/0043207 | A1 | 2/2020 | Lo et al. |
| 2020/0046431 | A1 | 2/2020 | Soper et al. |
| 2020/0046436 | A1 | 2/2020 | Tzeisler et al. |
| 2020/0054399 | A1 | 2/2020 | Duindam et al. |
| 2020/0060771 | A1 | 2/2020 | Lo et al. |
| 2020/0069192 | A1 | 3/2020 | Sanborn et al. |
| 2020/0077870 | A1 | 3/2020 | Dicarlo et al. |
| 2020/0078095 | A1 | 3/2020 | Chopra et al. |
| 2020/0078103 | A1 | 3/2020 | Duindam et al. |
| 2020/0085514 | A1 | 3/2020 | Blumenkranz |
| 2020/0109124 | A1 | 4/2020 | Pomper et al. |
| 2020/0129045 | A1 | 4/2020 | Prisco |
| 2020/0129239 | A1 | 4/2020 | Bianchi et al. |
| 2020/0138515 | A1 | 5/2020 | Wong |
| 2020/0155116 | A1 | 5/2020 | Donhowe et al. |
| 2020/0170623 | A1 | 6/2020 | Averbuch |
| 2020/0170720 | A1 | 6/2020 | Ummalaneni |
| 2020/0179058 | A1 | 6/2020 | Barbagli et al. |
| 2020/0188038 | A1 | 6/2020 | Donhowe et al. |
| 2020/0205903 | A1 | 7/2020 | Srinivasan et al. |
| 2020/0205904 | A1 | 7/2020 | Chopra |
| 2020/0214664 | A1 | 7/2020 | Zhao et al. |
| 2020/0229679 | A1 | 7/2020 | Zhao et al. |
| 2020/0242767 | A1 | 7/2020 | Zhao et al. |
| 2020/0275860 | A1 | 9/2020 | Duindam |
| 2020/0297442 | A1 | 9/2020 | Adebar et al. |
| 2020/0315554 | A1 | 10/2020 | Averbuch et al. |
| 2020/0330795 | A1 | 10/2020 | Sawant et al. |
| 2020/0352427 | A1 | 11/2020 | Deyanov |
| 2020/0364865 | A1 | 11/2020 | Donhowe et al. |

FOREIGN PATENT DOCUMENTS

| | | |
|---|---|---|
| CZ | 486540 B1 | 9/2016 |
| CZ | 2486540 B6 | 9/2016 |
| CZ | 2709512 B6 | 8/2017 |
| CZ | 2884879 B1 | 1/2020 |
| EP | 3413830 A4 | 9/2019 |
| EP | 3478161 A4 | 2/2020 |
| EP | 3641686 A2 | 4/2020 |

(56) References Cited

FOREIGN PATENT DOCUMENTS

| EP | 3644885 A1 | 5/2020 |
| EP | 3644886 A1 | 5/2020 |
| MX | 03005028 A | 1/2004 |
| MX | 225663 B | 1/2005 |
| MX | 226292 B | 2/2005 |
| MX | 246862 B | 6/2007 |
| MX | 265247 B | 3/2009 |
| MX | 284569 B | 3/2011 |
| WO | 2019006028 A1 | 1/2019 |

OTHER PUBLICATIONS

Communication pursuant to Article 94(3) EPC issued in European Application No. 20191559.2 dated Oct. 11, 2023.

* cited by examiner

SYSTEMS AND METHODS FOR DISPLAYING MEDICAL VIDEO IMAGES AND/OR MEDICAL 3D MODELS

CROSS-REFERENCE TO RELATED APPLICATION

The present application is continuation of U.S. patent application Ser. No. 16/892,598 filed Jun. 4, 2020, now allowed, which claims the benefit of and priority to U.S. Provisional Patent Application Ser. No. 62/888,892, filed on Aug. 19, 2019, the entire content of which is incorporated herein by reference.

FIELD

This disclosure relates to the field of displaying and/or providing user interaction with live and recorded two-dimensional (2D) or three-dimensional (3D) medical video images captured during a medical procedure and/or 3D models of a patient's anatomy.

BACKGROUND

Computer-assisted surgical systems, which may include image-guided surgical systems (e.g., systems for performing video-assisted thoracoscopic surgery (VATS)), and robotic surgical systems (e.g., systems for performing robot-assisted thoracoscopic surgery (RATS)), have allowed surgeons to more effectively treat tissue in a minimally invasive manner. Some computer-assisted surgical systems utilize three-dimensional models of a patient's anatomy, which may be based on pre-operative or intra-operative medical imaging (e.g., x-ray computed tomography (CT) or magnetic resonance imaging (MM)). And some computer-assisted surgical systems are used in conjunction with other objects in the surgical field (e.g., surgical instruments, robotic manipulators, or end effectors). The computer-assisted surgical systems have also revolutionized the way in which surgeons plan for surgical procedures and provide the surgeon with much-needed feedback during the course of a surgical procedure.

SUMMARY

This disclosure is directed to systems and methods for intraoperatively playing back and interacting with recorded video images captured earlier in the surgical procedure.

In one aspect, this disclosure features an intraoperative method. The intraoperative method includes: capturing, by a video camera, video images; recording at least a portion of the captured video images; displaying the at least a portion of the recorded video images and current video images captured by the video camera. The intraoperative method also includes: receiving a signal to highlight an anatomic structure; determining the positions of the anatomic structure in the at least a portion of the recorded video images; receiving a signal to highlight the anatomic structure; and highlighting the anatomic structure in the at least a portion of the recorded video images based on the determined positions, in response to the signal to highlight the anatomic structure. In aspects, the method may include determining that the highlighted anatomic structure is outside of a window; and, in response to determining that the highlighted anatomic structure is outside of the window, displaying an object in the window indicating the direction of the position of the highlighted anatomic structure or the direction of a recorded video image that contains at least a portion of the highlighted anatomic structure.

In aspects, implementations of this disclosure may include one or more of the following features. The video camera may be a laparoscopic video camera or an endoscopic video camera. The method may also include receiving a signal indicating selection of at least one of the current video images. Recording the at least a portion of the captured video images may include recording the selected at least one of the current video images. The current video images may be displayed in a first window and the at least a portion of the recorded video images may be displayed in a second window, which may be smaller than the first window and which may be overlaid on the first window. The second window may be overlaid on a corner portion or a quadrant of the first window. A time stamp or an annotation may be displayed in the first window or in the second window. The at least a portion of the recorded video images may be displayed as semitransparent video images overlaid on the current video images.

The method may also include displaying forward or backward movement through the recorded video images in response to a signal to move through the recorded video images in a forwards or backwards direction, respectively, while displaying the current video images.

In another aspect, this disclosure features a method for intraoperatively displaying three-dimensional (3D) video images of a patient, the method including: capturing, by a 3D video camera, 3D video images; and recording at least a portion of the captured 3D video images. The method also includes displaying at least one of the recorded 3D video images and current 3D video images captured by the 3D video camera. The method also includes generating a 3D model based on the captured 3D video images. The method also includes receiving a signal to change a field of view of the recorded 3D video images. The method also includes changing a field of view of the recorded 3D video images based on the 3D model and the received signal.

In aspects, implementations of this disclosure may include one or more of the following features. Changing the field of view may include rotating the field of view, zooming in or out of the field of view, or translating the field of view. The method may also include determining that the difference between the field of view of a recorded 3D video image and a field of view of a current 3D video image is greater than a first threshold. The method may also include in response to determining that the difference is greater than a threshold, indicating the direction to move the field of view of the recorded 3D video image so that the field of view of the recorded 3D video image aligns with the field of view of the current 3D video image and displaying a message not to move a surgical tool.

The method may also include determining that the difference between a field of view of a recorded 3D video image and a field of view of a current 3D video image is greater than a first threshold. The method may also include in response to determining that the difference is greater than a threshold, tracking the position of a surgical tool shown in the field of view of the current 3D video image and determining that the surgical instrument may be approaching an anatomic structure or has moved outside of the field of view of the current 3D video image. The method may also include in response to determining that the surgical instrument is approaching an anatomic structure or has moved outside of the field of view of the current 3D video image, generating a user notification.

The method may also include determining that a structure of interest in the recorded 3D video image is at least partially occluded by at least one other anatomic structure in the current field of view. The method may also include receiving a signal to view the structure of interest. The method may also include removing or making transparent or semitransparent the at least one other anatomic structure in the current field of view to make the structure of interest visible in response to determining that a structure of interest in the recorded 3D video image is at least partially occluded by at least one other anatomic structure in the current field of view and in response to receiving a signal to view the structure of interest.

The method may also include making the 3D model opaque in the current field of view to show internal anatomic structures or the location of previously placed fiducial markers. The method may also include recording the 3D model at time iterations. The method may also include detecting an instrument in the 3D model. The method may also include iteratively determining the position of the instrument. The method may also include iteratively recording the position of the instrument in association with the 3D model. The method may also include detecting an instrument in the 3D model. The method may also include iteratively determining the positions of the body and the tip of the instrument. The method may also include iteratively recording the determined position of the body and the tip in association with the 3D model. The method may also include displaying an indication of the determined position of the body and the tip over time.

The method may also include determining that at least a portion of a current 3D video image has changed with respect to a previous 3D video image. The method may also include in response to determining that at least a portion of the current 3D video image has changed with respect to the previous 3D video image, skipping the recording of the 3D model at the current time iteration or a subsequent time iteration. The method may also include recording a time stamp with each recorded 3D model. The method may also include calculating a difference between a current time stamp and a previous time stamp to determine the amount of time that has passed between recordings of the 3D model.

The method may also include detecting an instrument in the 3D model. The method may also include removing the instrument from the 3D model to obtain a modified 3D model. The method may also include displaying recorded 3D video images based on the modified 3D model. The 3D model may be a second 3D model. The method may also include the method may also include generating a first 3D model based on computed tomography (CT) or magnetic resonance imaging (MM) images of the patient. The method may also include the second 3D model may be generated based on the recorded 3D video images and the first 3D model. The method may also include highlighting those portions of the second 3D model that may be based on only the first 3D model.

In another aspect, this disclosure features an intraoperative method including: capturing, by a video camera, live video images; recording at least a portion of the live video images; and displaying the recorded video images and the live video images. The intraoperative method also includes displaying a representation of an instrument overlaid on the live video images. The intraoperative method also includes receiving movement commands from a remote computing device. The intraoperative method also includes moving the representation of the instrument according to the received movement commands.

In aspects, implementations of this disclosure may include one or more of the following features. The method may also include displaying movement through or change in orientation of the recorded 3D video images in response to a signal. The method may also include adding a representation of an instrument or annotations to the recorded 3D video image in response to a signal. The method may also include permanently adding or overlaying the representation of the instrument or the annotations to the live video images in response to a signal to return to the live video images.

In another aspect, this disclosure features a system including: a three-dimensional (3D) video camera configured to capture intraoperative 3D video images; and a processor and a memory having stored thereon instructions, which when executed by the processor causes the processor to: record at least a portion of the intraoperative 3D video images; create a 3D model based on the recorded 3D video images; receive a signal to change a viewpoint of the recorded 3D video images; change the viewpoint of the recorded 3D video images based on the 3D model and the received signal. The system also includes a display configured to display at least one of the recorded 3D video images and current 3D video images captured by the 3D video camera. The system also includes a user input device configured to transmit user input to change the viewpoint of the recorded 3D video images to the processor.

In another aspect, this disclosure features a system including: a video camera configured to capture video images during a surgical procedure; and a processor and a memory having stored thereon instructions, which, when executed by the processor, cause the processor to: record at least a portion of the captured video images to obtain recorded video images; receive a signal highlighting an anatomic structure in one recorded video image of the recorded video images; detect and highlight the anatomic structure in the recorded video images; and receive a signal to display at least one of the recorded video images with the highlighted anatomic structure. The system also includes a display configured to display the at least one of the recorded video images and current video images captured by the video camera.

BRIEF DESCRIPTION OF DRAWINGS

Various aspects of the disclosure are described hereinbelow with references to the drawings, wherein.

DETAILED DESCRIPTION

Figure 1:
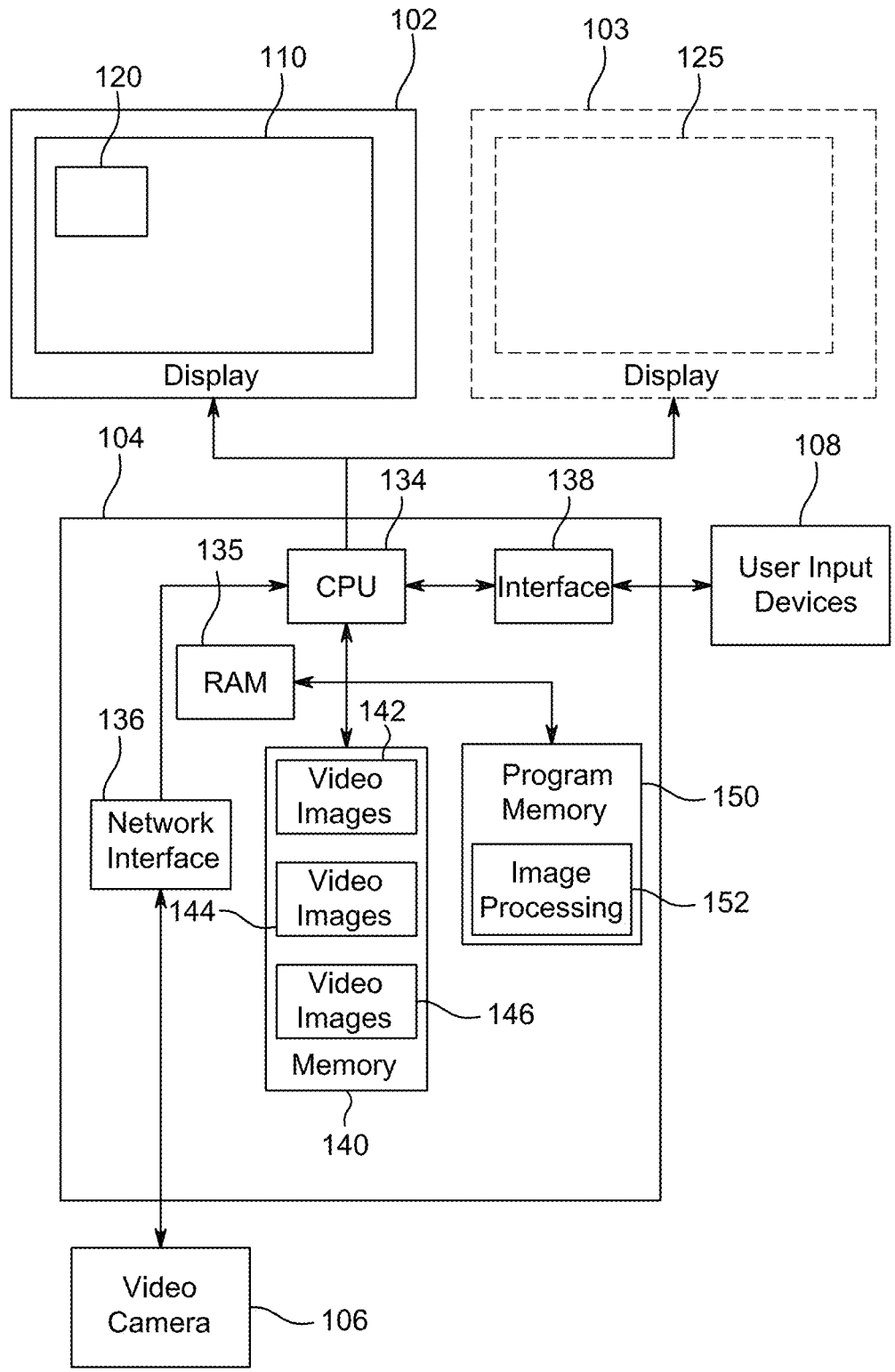
FIG. 1 is a schematic diagram of a computer-assisted surgical system for displaying and interacting with video images during a surgical procedure in accordance with the disclosure.

Laparoscopic tower systems include computer-based units or consoles that can record laparoscopic camera video for post-operative review. These systems, however, do not allow a clinician or surgeon to intra-operatively look back at or interact with camera video from an earlier time or period in a surgical procedure. A surgeon, for example, may wish to refer to a timepoint or period before a particular dissection to verify anatomic landmarks that may have moved because of dissection or resection or to compare a previous state with a current state.

According to some aspects of the disclosure, a surgeon may mark one or more time points or key frames in recorded video that can be returned to later during or after a surgical procedure, for example, by scrolling backwards through the recorded video. The recorded video may be presented to the clinician in a picture-in-picture format, where, for example, the recorded video is displayed in a small window that is incorporated into (e.g., overlaid on or inset in) a large window displaying current video. In some aspects, the recorded video may be displayed in a corner of the computer display or monitor and/or may be displayed with or without time stamps and other annotations. In aspects, the recorded video can be overlaid on the current video (e.g., the current endoscopic video) as a ghost or in a semitransparent or translucent manner to show the changes that have occurred over the period of the surgical procedure.

In a recorded video window, the surgeon may replay the recorded video forwards and backwards in time. In some aspects, the surgeon may also highlight an anatomic structure, e.g., a ureter, in a recorded frame of the recorded video (e.g., when the surgeon or other clinician scrolls to the recorded frame by moving the slide button in a slide bar or by utilizing any other suitable user control for browsing recorded frames of recorded video) or as the recorded video is replayed. For example, the surgeon may draw a line or a shape around a portion of a lung to be resected in a recorded frame of the recorded video during, for example, a lobectomy, a wedge resection to diagnose or treat small lung nodules, or a lung biopsy.

In some aspects, the specific anatomic structure may be detected, identified, or recognized (e.g., via any suitable image processing technique) and highlighted in all or a portion of the video frames or images in which the specific anatomic structure is detected, identified, or recognized. In some aspects, the specific anatomic structures may be highlighted in all or a portion of the recorded video frames or images in which the specific anatomic structure is in view, when requested by the surgeon. In further aspects, when an annotated or highlighted anatomic structure is out of view, an object (e.g., an arrow), or annotation (e.g., a pop-up message), or any other suitable indicator may be displayed in the recorded video window indicating the direction of the anatomic structure (e.g., left, right, up, down, forwards, and/or backwards).

In some aspects, a three-dimensional (3D model) may be generated based on 3D video images output from a 3D endoscope and the generated 3D model may be recorded. In other aspects, the 3D model may be generated based on preoperative images (e.g., computed tomography (CT) images from a CT scan of a patient). In additional aspects, as the 3D endoscope (a) views new anatomy, (b) views already-scanned anatomy from a new vantage point, or (c) views the already-scanned anatomy after it has been modified by the surgical procedure, the 3D model may be updated with currently-captured 3D video images and the updated 3D model may be recorded. In aspects, the updated 3D model may be recorded with previously recorded 3D models or a previously recorded 3D model may be overwritten by the updated 3D model. In aspects, the clinician can change (e.g., rotate) the viewpoint of the previously recorded or saved 3D video images. This change (e.g., rotation) may bring highlighted structures back into view, if that structure had been viewed at some time earlier or later in the surgery. The clinician (e.g., surgeon) may highlight the structure during the surgical procedure and the system may track the structure in the video images both forwards and backwards in time. The clinician may also change the viewpoint (e.g., rotate the viewpoint) to realign the current field of view (FOV) with a previous FOV in the surgical procedure even if the video camera FOV has changed or moved between the current FOV and the previous FOV.

The 3D model allows the surgeon or other clinician to review the recorded video images from a specific viewpoint regardless of the motion of the 3D endoscope or video camera. To achieve this, the 3D model is stored at specific iterations of time. In some aspects, if the scene does not change between scheduled save iterations, subsequent save iterations are skipped until a change in the scene occurs. This feature may be utilized to conserve memory space or processing resources. In further aspects, each iteration or frame in which a save occurs may be accompanied by a time stamp to indicate the amount of time that has passed between save iterations.

The system may remove one or more surgical instruments from the saved 3D model to prevent occlusion of anatomic structures shown in the saved 3D model. The location of the surgical instruments may also be saved for post-operative review. The instrument body and/or instrument tip may be tracked by the system for later use, e.g., for surgical skill analysis or training.

In some aspects, using telepresence, phantom instruments operated or moved by a user may also be introduced into the live view during the surgical procedure. As such, this user may be remote from the surgery. In further aspects, a remote user can also control moving the surgical view back in time or change orientations while adding phantom instruments or annotations. In additional aspects, any added annotations can then become permanent when the view is returned to the present time or orientation automatically or upon selection.

The 3D model created from the 3D endoscopic video images may be combined with the patient's CT model, which is based on the patient's CT scan, to fill in missing portions of the 3D endoscopic model. In some aspects, the system may include a method of display (e.g. color or overlaid pattern) to designate portions of the 3D model that are from the CT model and not generated from the endoscopic 3D model.

Should the person viewing the recorded 3D image change their view (e.g., via rotation, zoom, or translation) such that the current endoscopic field of view (FOV) is not displayed, the systems of this disclosure may highlight the direction needed to return to the current FOV and may provide a user warning to prevent motion of surgical tools until they are again within the current FOV. In some aspects, while the current user view does not overlap the actual current endoscopic FOV, any motion of surgical instruments within the current endoscopic FOV is tracked and the user is notified if an instrument is approaching any anatomic structure or has moved outside of the current endoscopic FOV. This functionality may be available for both manual video-assisted thoracoscopic surgery (VATS) and robot-assisted thoracoscopic surgery (RATS). In the case of RATS, surgical instrument motion may be limited by the robotic system when the user FOV and the endoscopic FOV do not match.

During the surgical procedure, as the endoscope FOV moves around the surgical cavity, the 3D model may continue to be built or updated. In aspects, reviewing the earlier 3D model as it was recorded earlier in the surgical procedure from a new FOV position may result in a structure of interest (e.g., a critical structure of interest) being occluded by anatomy that is in the current FOV, but was not part of the original FOV (e.g., the video camera may have traveled around a structure of interest so that the video camera is looking at what was the backside earlier in the surgical procedure). The clinician may select a setting or button to ghost out the foreground anatomy in order to see the original structure of interest from the new FOV. Ghosting out the foreground anatomy includes making the foreground anatomy translucent or otherwise modifying the foreground anatomy so that structures of interest behind the foreground anatomy are made visible. At any time, the recorded 3D model can be made opaque to show internal anatomic structures or fiducial markers placed prior to surgery. The location and structure of the internal anatomic structures or fiducial markers may be captured during pre-surgical modeling of the patient's diagnostic CT scan.

FIG. 1 is a schematic diagram of a visualization system according to aspects of this disclosure. The system includes a display 102, a computing device 104, a video camera 106, and one or more user input devices 108. The medical video camera 106 is configured to traverse through passages or cavities within the body during a surgical procedure. The video camera 106 may include a laparoscope, an endoscope, a three-dimensional (3D) endoscope for capturing 3D video images, or any other device suitable for capturing images or video inside a patient. The computing device 104 receives video images captured by the video camera 106, records all or a portion of the captured video images, and causes the display 102 to display currently captured video images in a first window 110. In some aspects, the computing device 104 also displays previously-recorded video images in a second window 120 at all times that the computing device 104 displays the currently captured video images, in response to user selection of a suitable user control (e.g., when the user selects the record button 216 illustrated in FIG. 2), or in response to a suitable triggering event (e.g., when a surgical tool is detected in the currently captured video images). As illustrated in FIG. 1, the second window 120 may overlap the first window, may be smaller in size than the first window 110, and may be displayed in a corner of the second window 120 to enable a user (e.g., a clinician or a surgeon) to view currently captured video images and recorded video images. Alternatively, the first window 110 and the second window 120 may be displayed side-by-side in display 102. Optionally, the system may include a second display 103, which displays the previously recorded video images in window 125. In another aspect, the second window 120 may be the same size or larger than the first window 110. For example, the second window 120 may be overlaid on the first window 110.

The computing device 104 includes a CPU 134, which executes programs or applications stored in program memory 150 (e.g., a solid-state drive and/or a hard disk drive), and/or random-access memory (RAM) 135. The programs may include instructions executable by the CPU 134 for executing the methods of this disclosure including the methods of FIGS. 6-11. The programs may include instructions to receive captured video images from the video camera 106 via a network interface 136 and store those video images 142 in data repository memory 140, which, in some aspects, may be separate from the program memory 150. The CPU 134 may also execute one or more programs stored in program memory 150 to build a 3D anatomic model 144 based on the recorded video images 142 and/or other suitable preoperative or postoperative images for building a suitable 3D anatomic model 144. In some aspects, the 3D anatomic model 144 may incorporate pre-operative CT images 146. The computing device 104 may be a stationary computing device, such as a personal computer, or a portable computing device such as a tablet computer. The computing device 104 may embed multiple computer devices.

The program memory 150 may store image processing programs 152, which, when executed by the CPU 134, cause the CPU 134 to perform image processing functions on the currently captured video images, the recorded or stored video images 142, and/or the 3D model. The image processing functions may include detecting an object, e.g., an instrument, and/or tracking an object, e.g., a highlighted anatomic structure, in the video images.

Data repository memory 140 and program memory 150 may include any non-transitory computer-readable storage media. In aspects, data repository memory 140 and program memory 150 may include one or more storage devices such as solid-state storage devices, e.g., flash memory chips. Alternatively, or in addition to the one or more solid-state storage devices, data repository memory 140 and program memory 150 may include one or more mass storage devices connected to the CPU 134 through a mass storage controller (not shown) and a communications bus (not shown).

Although the description of computer-readable media contained herein refers to solid-state storage, it should be appreciated by those skilled in the art that computer-readable storage media can be any available media that can be accessed by the CPU 134. That is, computer readable storage media may include non-transitory, volatile and non-volatile, removable and non-removable media implemented in any method or technology for storage of information such as computer-readable instructions, data structures, program modules or other data. For example, computer-readable storage media may include RAM, ROM, EPROM, EEPROM, flash memory or other solid-state memory technology, CD-ROM, DVD, Blu-Ray or other optical storage, magnetic cassettes, magnetic tape, magnetic disk storage or other magnetic storage devices, or any other medium which may be used to store the desired information.

The network interface 136 may be configured to connect to a network such as a local area network (LAN) including a wired network and/or a wireless network, a wide area network (WAN), a wireless mobile network, a Bluetooth network, and/or the Internet. Network interface 136 may be used to connect to a computed tomography (CT) scanner (not shown) or a magnetic resonance imaging (Mill) scanner (not shown). User input devices 108 may include any device by which a user may interact with workstation computing device, such as, for example, a mouse, keyboard, foot pedal, touch screen, and/or voice interface. Interface 138 may include any connectivity port or bus, such as, for example, parallel ports, serial ports, universal serial busses (USB), or any other similar connectivity port known to those skilled in the art. The user input devices 108 may include a keyboard, a mouse, a microphone, or a touchscreen, which allows a user (e.g., a clinician) to interact with the currently captured video images and the recorded video images. For example, the second window may include controls, which allow the user to scroll through previously recorded video images or change the field of view of previously recorded 3D video images based on the 3D model 144.

Figure 2:
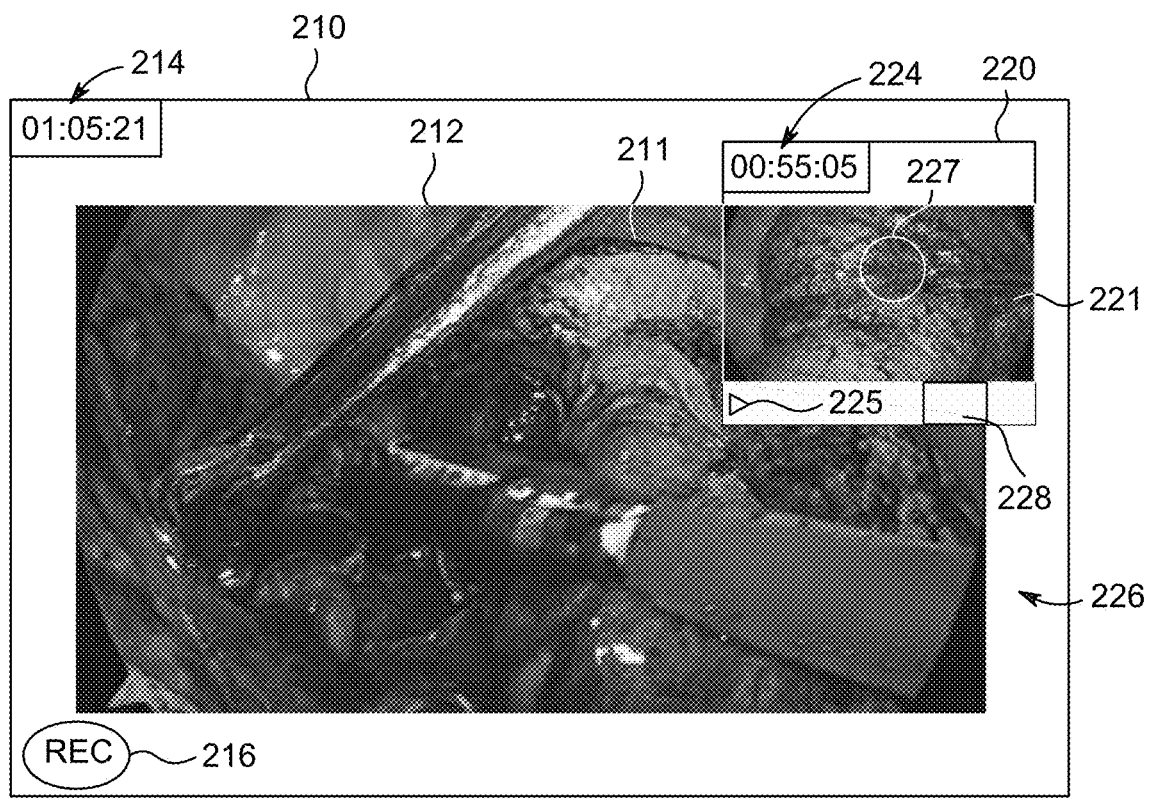
FIG. 2 is a screen shot of an example of a user interface for playing and interacting with recorded video images in accordance with the disclosure.

FIG. 2 is a screen shot of an example of a user interface for playing and interacting with recorded video images in accordance with the disclosure. As illustrated, a first window 210 and a second window 220 may be displayed on the display 102 of FIG. 1. The first window 210, which is larger than the second window 220, may include a live video camera view 212 showing live video images 211 while the second window 220 may include a recorded video camera view 222 showing previously recorded video images 221. In other aspects, the live video camera view 212 may be shown in the second window 220 while the previously recorded video camera view 222 may be shown in the first window 210.

As illustrated in FIG. 2, the first window 210 may include a current time field 214, which displays a current time obtained from a running clock or timer. The running clock or timer may be reset and started at the beginning of each surgical timer. The current time may be applied as a time stamp to each live video image that is recorded. The second window 220 may also show the time stamp 224 of the recorded video image 221. The second window 220 includes a play button 225, which starts and stops the playback of the recorded video images 221 in the recorded video camera view 222, a scroll bar 226, and a user control 228 that allows a user to scroll through the recorded video images 221. Any suitable controls, icons, or buttons may be associated with the second window 220 for controlling or otherwise interacting with the recorded video camera view 222. The user may also place objects, e.g., object 227, on the recorded video image 221 to mark or highlight structures (e.g., anatomic structures) in the recorded video image 221. The object 227 may be applied to the recorded video image 221 permanently, temporarily until the object 227 is selected again or unselected, temporarily for a predetermined or preset period, or for any other suitable period.

Alternatively, or additionally, the user may overlay one or more objects on the currently captured video images 211 in the first window 210. If, at the same time, the record button 216 is selected or the live video camera view 212 is selected to start recording the currently captured video images 211, the video images 211 may be recorded with the one or more objects overlaid on the recorded video images 221.

Figure 3:
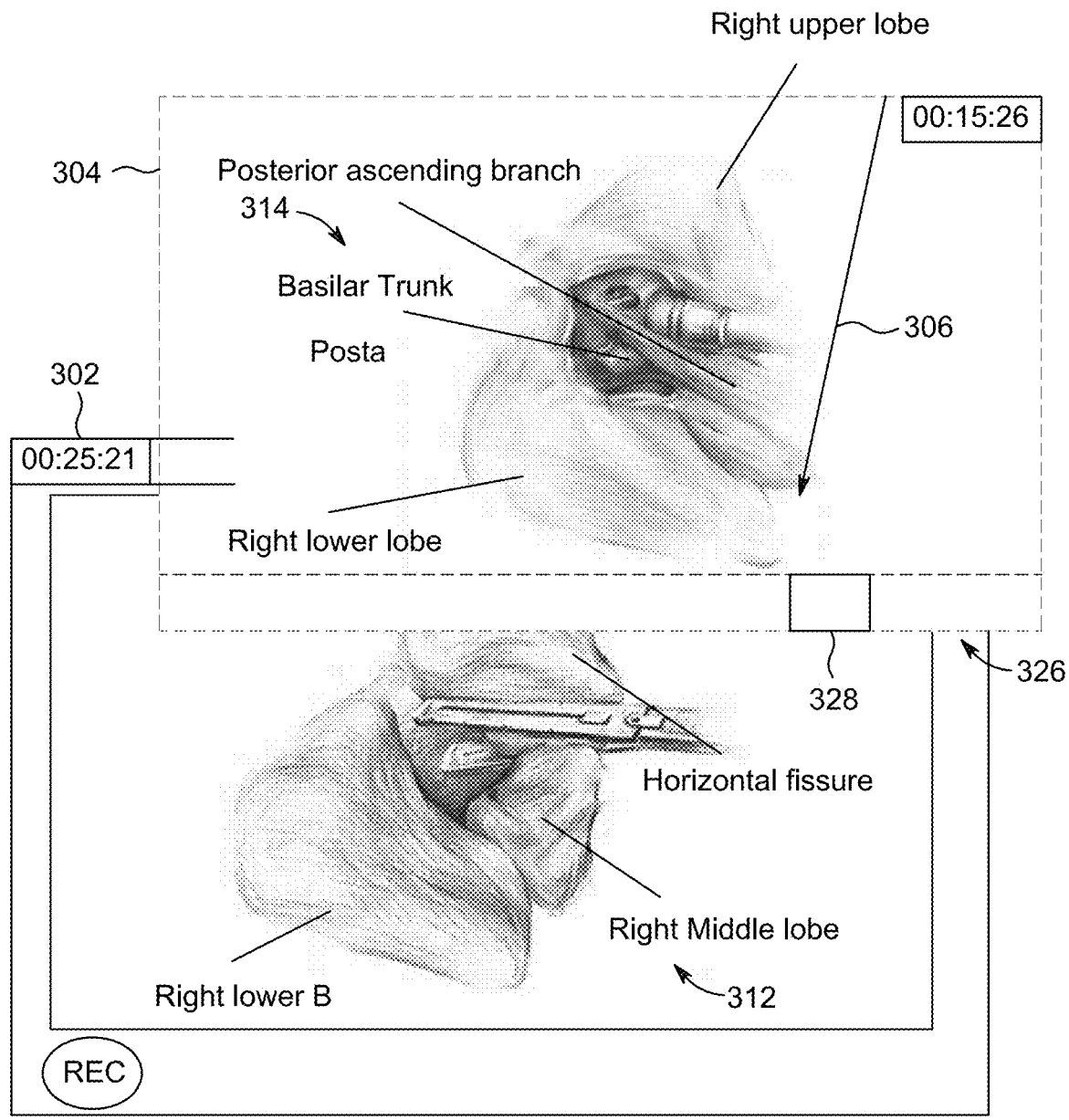
FIG. 3 is an exploded view of a screen shot of an example of a user interface illustrating how recorded video images are overlaid on current video images in accordance with the disclosure.

FIG. 3 illustrates a screen in which a second window 304 for displaying recorded video images is overlaid 306 on a first window 302 for displaying live video images. The second window 304 and the recorded video images 314 may be semitransparent or translucent so that the live video images 312 in the first window 302 are visible. The second window 304 includes a scroll bar 326 and a user control 328, which, when selected and moved right or left along the scroll bar 326, allows a user to scroll through recorded video images 314 while viewing the live video images 312 in the first window 302. The second window 304 also includes a scroll bar 326 with a user control 328, which, when moved along the scroll bar 326, causes previous or subsequent images to be displayed in the second window 304.

Figure 4A:
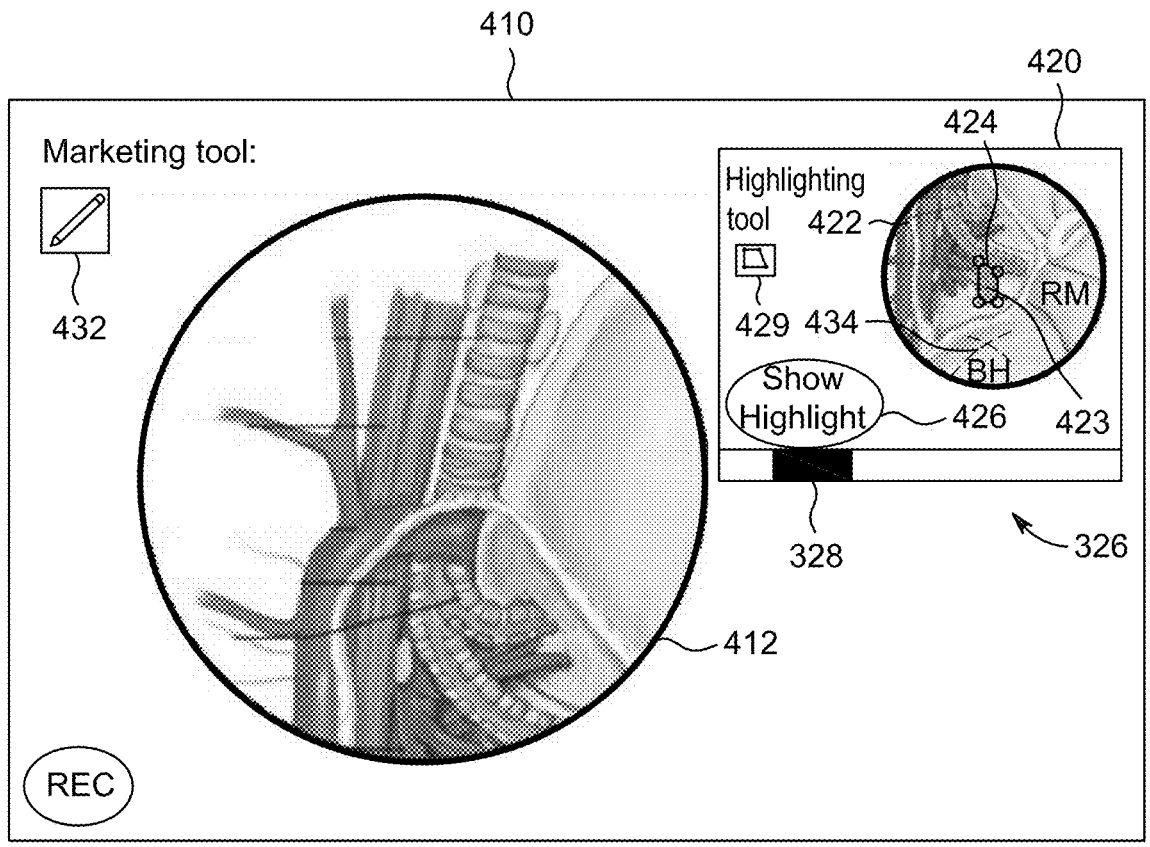
FIGS. 4A and 4B are screen shots taken at different times of still another example of a user interface for navigating through and interacting with three-dimensional (3D) video images in accordance with the disclosure.
Figure 4B:
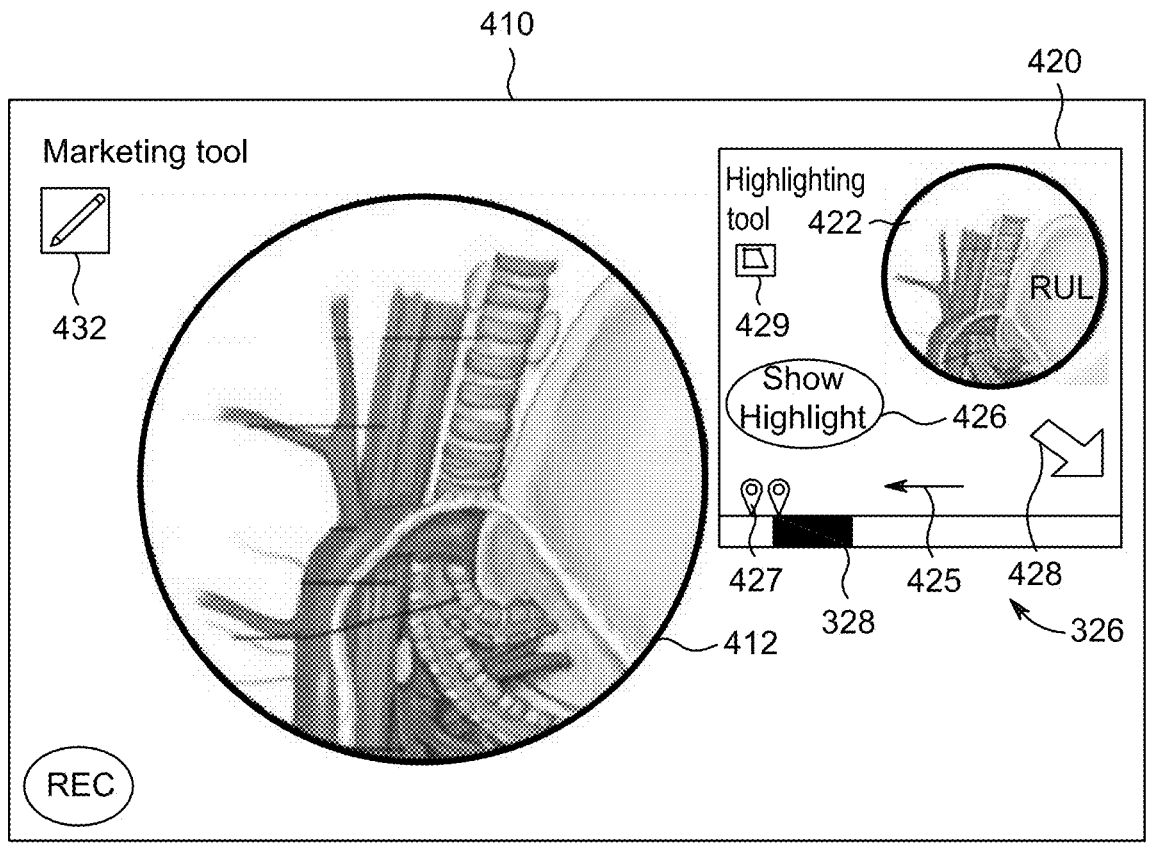

FIGS. 4A and 4B illustrate a user interface that includes a first window 410 configured to display live 3D video images 412 and a second window 420 configured to display recorded 3D video images 422 and allows a clinician to change the view of the recorded 3D video images 422 regardless of the motion of the video camera. To accomplish this, a 3D model may be generated and integrated into the recorded 3D video images 422. The 3D model may be generated based on preoperative images such as computed tomography (CT) or magnetic resonance imaging (Mill) images. As shown in FIG. 4A, the second window 420 shows a laparoscopic video image 422 and includes a highlighting button 429, which may be selected by the user to place a polygon around or outlining an anatomic structure. For example, the user may select the highlighting button 429 and may place and move the points of a polygon 424 so that the polygon 424 surrounds the right lower lobe bronchus 423. The second window 420 also includes a "Show Highlight" button 426, which may be selected to toggle between hiding and showing the polygon 424.

In some cases, the user may move to previously recorded video images in the second window 420 that do not include the highlighted anatomic structure. For example, as shown in FIG. 4B, the user may move user control 328 to the left to view previously recorded video images. This changes the field of view so that the polygon 424 is no longer visible in the laparoscopic view 422. When the "Show Highlight" button 426 is toggled on, the second window 420 may display an arrow object 428 outside of the perimeter of the laparoscopic view 422 indicating the direction of the polygon 424 with respect to the previously-recorded video image in the laparoscopic view 422 shown in FIG. 4B. Additionally or alternatively, the second window 420 may display an arrow 425 above the scroll bar 326 indicating the direction of the recorded video image or images that contain the polygon 424 and/or may display one or more marks 427 indicating the recorded video images or range of recorded video images that contain the polygon 424, which may highlight an anatomic feature.

Figure 5:
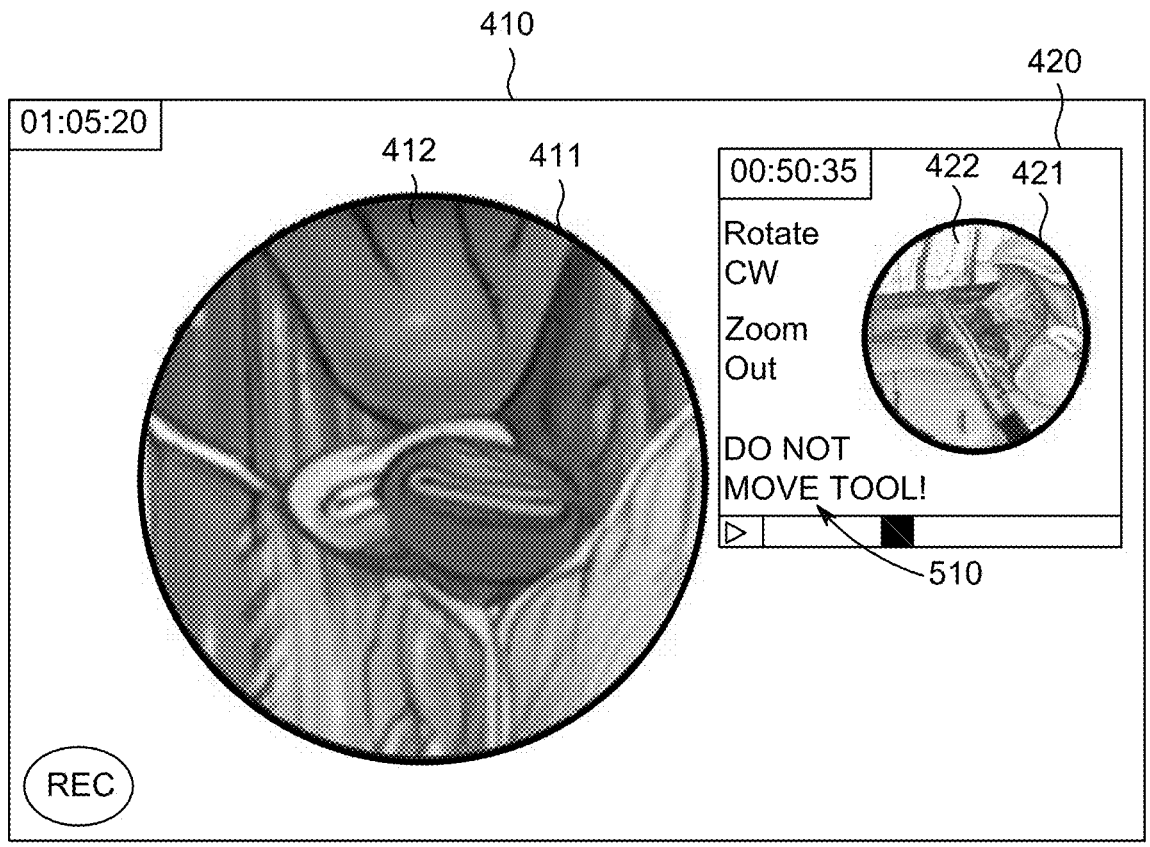
FIG. 5 is a screen shot of another example of a user interface for displaying live and recorded 3D video images in accordance with the disclosure.

FIG. 5 is a screen shot of still another example user interface for interacting with live and recorded 3D video images in accordance with the disclosure. In this aspect, messages 510 are displayed to the user indicating how field of view of the recorded 3D video image 422 should be changed so that the field of view of the recorded 3D video image 422 is the same as or similar to the field of view of the live 3D video image. As illustrated in the example of FIG. 5, the messages 510 include "Rotate CW" and "Zoom Out". In some aspects, the messages 510 may be hidden when, for example, a button or any other suitable user control is selected by the user. The user may then use an input device, e.g., a keyboard and/or a mouse, to rotate clockwise and zoom out in the field of view of the recorded 3D video image 422. In aspects, the messages 510 may also include a "DO NOT MOVE TOOL!" message to warn the clinician not to move the surgical tool in the live 3D video images 412 while the field of view of the recorded 3D video images 422 is being changed so that alignment of the field of view of the recorded 3D video image 422 and the field of view of the live 3D video image 412 can be properly completed. This resets the field of view of the recorded 3D video image 422 to the field of view of the live 3D video images 412 so that the clinician can use the recorded 3D video image to plan or simulate the next steps of the surgical procedure in the second window using the field of view of the live 3D video images 412 as a starting point. In some aspects, a third window may be displayed (e.g., on display 102 or display 103 of FIG. 1) showing the 3D model as described herein. The 3D model may also be used by the clinician to plan or simulate the next steps of the surgical procedure or to visualize anatomical features that are not visible in the live or recorded 3D video images 412, 422.

Figure 6:
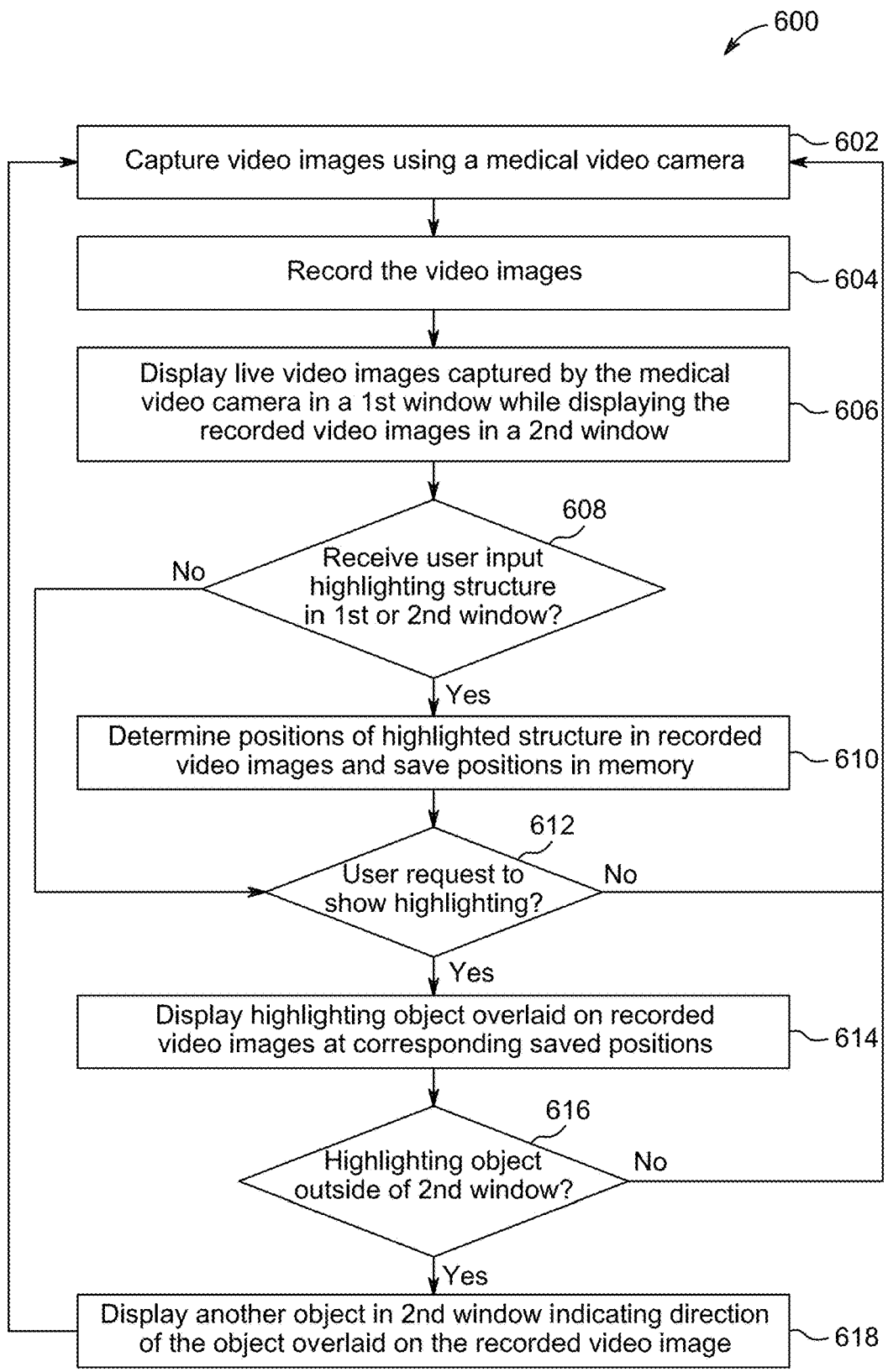
FIGS. 6-12 are flow charts illustrating examples of methods of displaying live and recorded video images in accordance with the disclosure.

FIG. 6 is a flowchart of a method of displaying live and recorded video images and tracking a highlighted anatomic feature or structure, which may be employed in a manner similar to that described above with respect to FIGS. 4A and 4B. At block 602, video images are captured using a medical video camera, such as a laparoscopic camera or a 3D endoscopic camera. As video images are being captured, they may be displayed in a first window (e.g., the first window 410 of FIG. 4A) as live video images (e.g., live video images 412). While the live video images are being displayed, the clinician may place marks at different locations on the live video images. For example, as illustrated in FIG. 4A, the clinician may select the marking tool button 432 to activate a freeform drawing tool and may draw a marking or an annotation on the live video images 412 using the freeform drawing tool. At block 604, the live video images captured by the medical video camera are recorded in memory. In those aspects in which the clinician places marks on the live video images, the marks may be recorded on or in association with the recorded video images so that the clinician can later find and view those marked, recorded video images. For example, as illustrated in FIG. 4A, a mark 434 previously drawn on the live video images 412 (e.g., to indicate a lobe to be surgically removed) may be recorded with and applied to the recorded video images 422.

In aspects, all or a portion of the captured video images may be recorded. At block 606, current or live video images captured by the medical video camera are displayed in the first window while the recorded video images are displayed in a second window. In some implementations, during normal operation only the first window may be shown on the display 102. Then, the clinician or other user may select a button or other user control to cause the second window to be shown on the display and/or overlaid on the first window, as illustrated in FIG. 1.

At block 608, a system processor, e.g., CPU 134, determines whether user input highlighting structure in the first or second window is received, e.g., via interface 138. When user input highlighting structure in the first or second window is received, positions of the highlighted structure in the recorded video images are determined and saved in memory, e.g., memory 140 of FIG. 1, at block 610. Then, at block 612, the system processor determines whether there is a user request to show the highlighting. If the result of the determination at block 612 is "Yes", a highlighting object is overlaid on the recorded video images at the corresponding saved positions at block 614. The highlighting object may be a circle surrounding the anatomic structure or an object outlining the edges of the anatomic structure shown in the recorded video images.

While a clinician is scrolling through or replaying the recorded video images, the highlighted structure may leave the field of view of the second window. In one implementation, an object may be displayed in the second window showing the direction of the structure with respect to the currently displayed recorded video images. Accordingly, at block 616, the system processor determines whether the highlighting object overlaid on the recorded video images is outside of the second window. If the result of the determination at block 616 is "Yes", another object (e.g., an arrow object 428) is displayed in the second window indicating the direction of the highlighting object, as illustrated in FIG. 4B. Then, the method 600 returns to block 602. If the result of the determinations at blocks 612 or 616 are "No", the method 600 returns to block 602.

Figure 7:
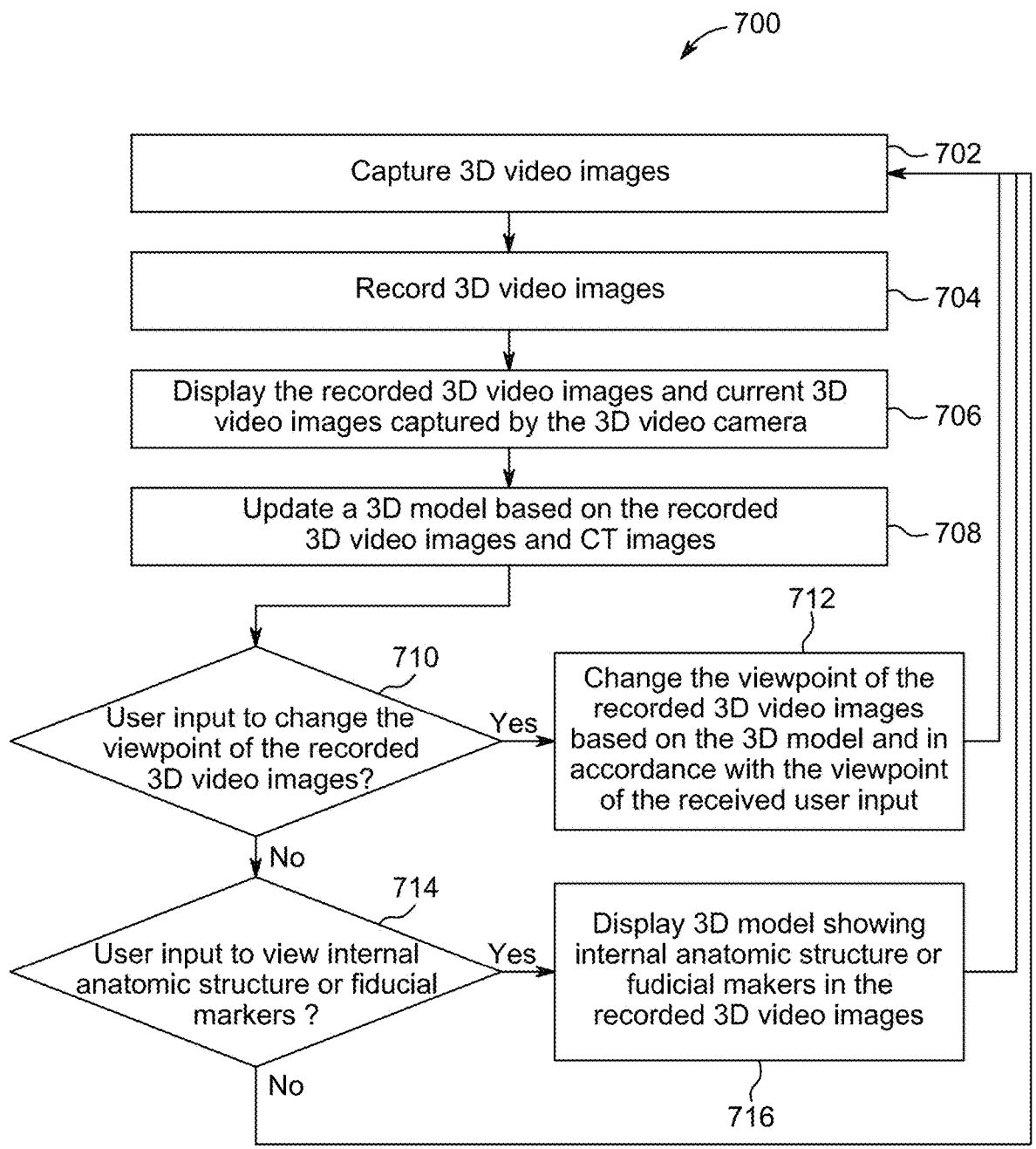

The systems and methods of this disclosure may also be applied to 3D video images captured by, for example, a 3D endoscope. FIG. 7 is a flowchart of an example method of displaying live and recorded 3D video images and generating a 3D model that is incorporated into the recorded 3D video images. At block 702, 3D video images are captured using a 3D video camera, such as a laparoscopic camera or a 3D endoscopic camera. As 3D video images are being captured, they may be displayed in a first window as live 3D video images. At block 704, the live 3D video images captured by the medical video camera are recorded in memory, e.g., a data repository memory 140 of FIG. 1.

At block 706, the recorded 3D video images are displayed in a second window at the same time that live 3D video images captured by the 3D video camera are displayed in the first window. In some implementations, during normal operation, only the live 3D video images may be shown on the display 102. Then, the clinician or other user may select a button or other user control in the display 102 to cause the recorded 3D video images to be shown on the display 102. At block 708, a 3D model is updated based on the recorded video images and computed tomography (CT) images, which may be combined with the recorded video images to fill in missing areas in the 3D model. The missing areas may include internal portions of anatomical features that are not visible to a video camera, e.g., a laparoscopic video camera.

At block 710, the system processor determines whether there is user input to change the viewpoint of the recorded 3D images. The user input may be to rotate the recorded 3D image so that the clinician can view one or more anatomic structures from a different perspective. For example, the clinician may want to view the backside of an anatomic structure. The user input may include clicking on and holding a cursor on a recorded 3D video image and moving the cursor to rotate the recorded 3D video image. If the result of the determination at block 710 is "Yes", the viewpoint of the recorded 3D video images is changed based on the 3D model and the viewpoint of the user input at block 712. For example, as the user moves the cursor to rotate the one or more anatomic structures in the 3D video image, new 3D video images corresponding to the new viewpoints are displayed based on the updated 3D model.

If the result of the determination at block 710 is "No", the method 700 includes determining, at block 714, whether there is user input to view an internal anatomic structure or one or more fiducial markers. If the result of the determination at block 714 is "Yes", a 3D model showing the internal anatomic structure or fiducial markers is displayed in the recorded 3D video images. For example, the 3D model may be overlaid on the recorded 3D video images or portions of the recorded 3D video images may be ghosted and the 3D model may be shown at the ghosted portions. If the result of the determination at block 714 is "No", the method 700 returns to block 702. Also, after blocks 712 and 716 are completed, the method 700 returns to block 702.

Figure 8:
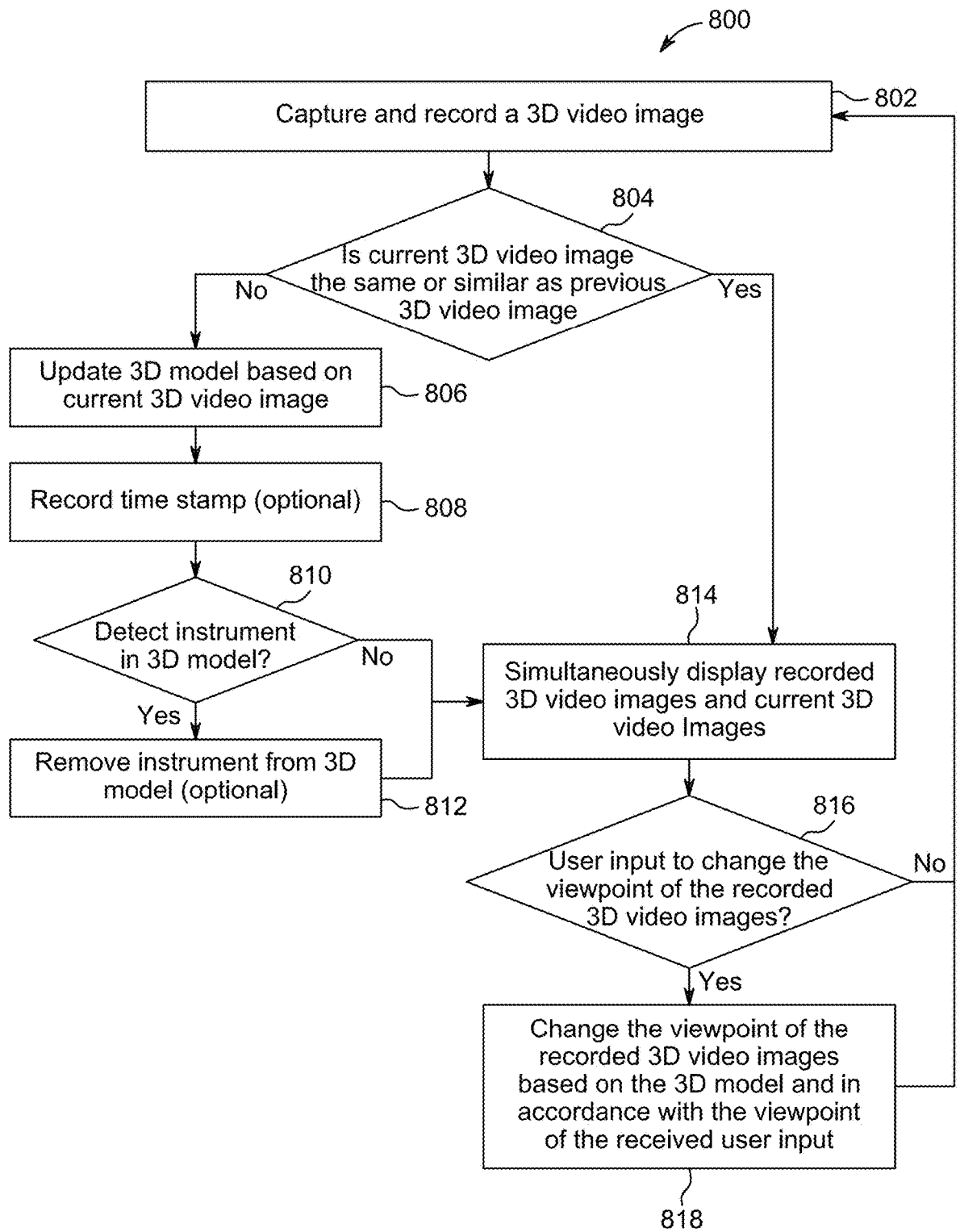

In aspects, various image processing functions may be performed, as illustrated in FIG. 8. After capturing and recording a 3D video images at block 802, the method 800 includes determining whether the current 3D video image is the same or similar as a previous 3D video image at block 804. Block 804 may include comparing the current and previous 3D video images using suitable image processing algorithms and determining whether the result of the comparison is greater than a predetermined threshold, which represents a sufficient difference between the current and previous 3D video images to warrant recording of the current 3D video image. If the result of the determination is "Yes", recorded 3D video images and current 3D video images are simultaneously displayed in accordance with the various aspects described in this disclosure.

If the result of the determination in block 804 is "No", a 3D model of the anatomical structures captured by the 3D video images is updated based on the current 3D video image at block 806, and a time stamp is optionally recorded in association with the updated 3D model at block 808. The time stamps associated with 3D model may be used to determine the rate at which the 3D model is updated or indicate the last time the 3D model was updated. In some aspects, if the result of the determination at block 804 is "No", the method 800 may further include recording the current 3D video image instead of recording the current 3D video image at block 802, which may save memory space by recording only the currently-captured 3D video images that are substantially different from the previously-captured 3D video images.

After recording a time stamp at block 808, the method 800 further includes determining whether an instrument (e.g., a stapler or a probe) is detected in the 3D model at block 810. If the result of the determination at block 810 is "Yes", the instrument is optionally removed from the updated 3D model at block 812 using one or more suitable image processing techniques and the method 800 proceeds to block 814. If the result of the determination at block 810 is "No", the recorded 3D video images and the current 3D video images are simultaneously displayed at block 814.

At block 816, the method 800 includes determining whether there is user input to change the viewpoint of the recorded 3D video images. For example, the user input may include clicking and holding a position on the recorded 3D video image, and dragging the cursor in direction to rotate the recorded 3D video image. Alternatively, the method 800 may include displaying buttons, which, when selected, rotate the recorded 3D video image about an x-, y-, or z-axis. If the result of the determination is "Yes" at block 816, the viewpoint of the recorded 3D video image is changed based on the 3D model and in accordance with the viewpoint of the received user input at block 818.

For example, when the clinician rotates the recorded 3D video image a given number of degrees (e.g., 5 degrees) about the z-axis, the 3D model is used to construct those portions of anatomical structures or features that are not visible in the previously recorded 3D video images. The constructed portions may then be integrated with the previously recorded 3D video image to generate a 3D video image that is rotated a given number of degrees about the z-axis. Various image processing techniques may be employed to ensure a smooth transition from the originally recorded 3D video image to the rotated 3D video image. In aspects, the user may perform functions in addition to or other than rotation, such as zooming in and out and/or translating or panning in a particular direction. After block 818 or if the result of the determination at block 816 is "No", the method 800 returns to block 802.

Figure 9:
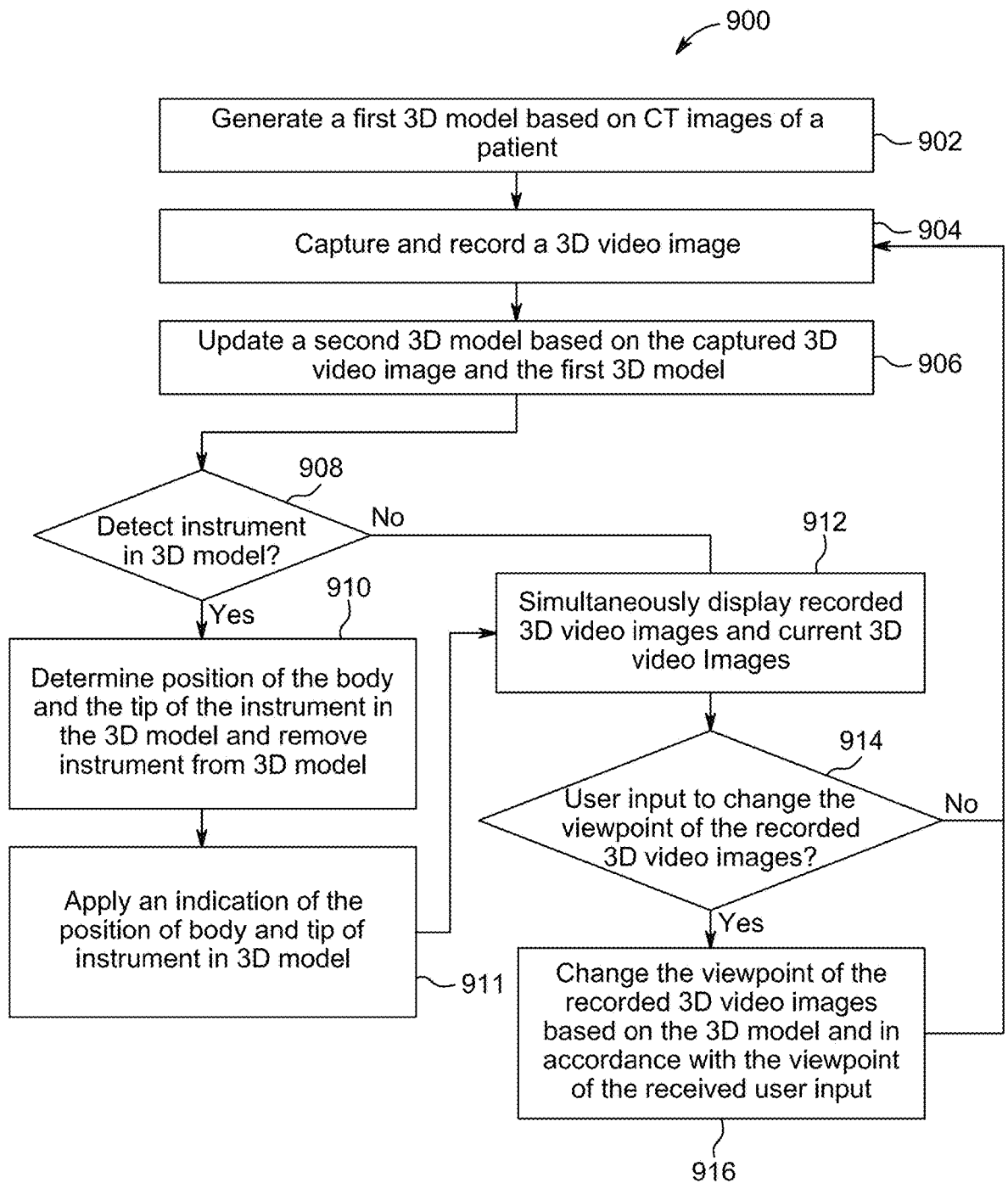

FIG. 9 illustrates another method 900 according to an aspect in which a 3D model is generated and incorporated into the record 3D video images. At block 902, a first 3D model is generated based on CT images of a patient. The CT images may be captured and the first 3D model may be generated based on preoperative CT images of the patient one or more days prior to a surgical procedure. After capturing and recording a 3D video images at block 904, the method 800 includes updating a second 3D model based on the captured 3D video image and the first 3D model at block 906. Block 906 may include aligning the captured 3D video image with the first 3D model, finding one or more differences between the captured 3D video image and the first 3D model, and using those differences to update the second 3D model.

After updating the second 3D model at block 906, the method 900 further includes determining whether an instrument (e.g., a stapler or a probe) is detected in the 3D model at block 908. If the result of the determination at block 908 is "Yes", the position of the body and tip of the instrument in the 3D model are determined and the instrument is removed from the updated 3D model at block 910 using one or more suitable image processing techniques so that the instrument does not obstruct the view of the 3D model. Then, at block 911, an indication of the position of the body and tip of the instrument are applied to the 3D model. The indication of the position of the body and tip of the instrument may include a crosshair mark or other similar mark at the center of the body of the instrument and at the tip. In this way, the instrument does not block or interfere with the view of the anatomical features in the 3D model, especially when the clinician is changing the viewpoint of the recorded 3D video images.

After block 911 or if an instrument is not detected in the 3D model at block 908 (in other words, if the determination at block 908 is "No"), the recorded 3D video images and the current 3D video images are simultaneously displayed at block 912. In some aspects, those portions of the recorded 3D video images, which are based on the first 3D model (e.g., a 3D model based on CT scan data) but not based on the captured 3D video images, may be highlighted or otherwise indicated on the recorded 3D video images, e.g., highlighted with a particular color or overlaid pattern. At block 914, the method 900 includes determining whether there is user input to change the viewpoint of the recorded 3D video images. If the result of the determination at block 914 is "Yes", the viewpoint of the recorded 3D video images is changed based on the 3D model and in accordance with the viewpoint of the received user input at block 916. After block 916 or if the result of the determination at block 914 is "No", the method 900 returns to block 904.

Figure 10:
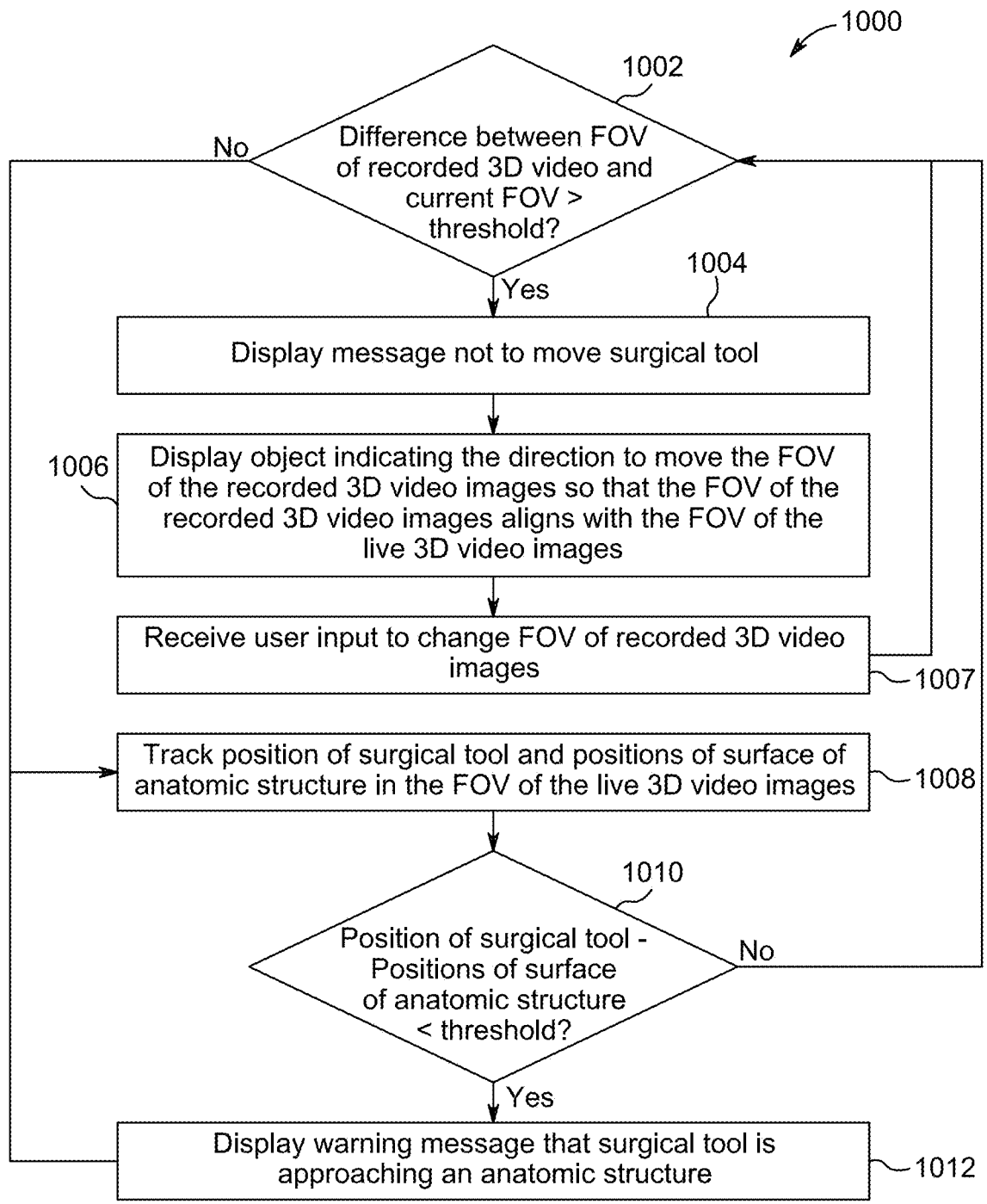

In some implementations, the methods of this disclosure may include features that track the differences between the currently viewed live video images and the currently viewed recorded video images and guide the clinician in aligning the currently viewed recorded video images with the currently-viewed live video images. The methods of this disclosure may also include features that track the position of a surgical tool (e.g., a blade) with respect to anatomical features in the live video images in order to ensure the safety of the patient. FIG. 10 illustrates a method 1000 that incorporates those features.

At block 1002, the method 1000 includes determining whether the difference between the field of view of recorded 3D video images and the current field of view of live 3D video images is greater than a threshold. Block 1002 may include performing image processing on both the live 3D video images and the recorded 3D video images currently being displayed to recognize features in those images, determining whether those images include the same features, and determining the distances between though same features. If none of the recognized features in the live 3D video images correspond to the recognized features in the recorded 3D video images, then a 3D model based on one or more preoperative images (e.g., CT images) may be used to determine how much the field of view of the currently-displayed recorded 3D video images needs to be changed so that the field of view of the currently-displayed recorded 3D video images is aligned with the field of view of the currently-displayed live 3D video images.

If the result of the determination at block 1002 is "Yes", a message is displayed not to move a surgical tool at block 1004. The message may be displayed in the same window in which the live 3D video images are displayed. At block 1006, an object (e.g., an object in the shape of an arrow) indicating the direction to move the field of view of the recorded 3D video images so that the field of view of the recorded 3D video images can align with the field of view of the live 3D video images is displayed. The user may then change the field of view of the recorded 3D video images by using a mouse to click on and move a cursor on the recorded 3D video image to bring the FOV of the recorded 3D video images in alignment with the live 3D video images at block 1007. Then, the method 1000 repeats blocks 1002-1007 until the difference between the current field of view of the recorded 3D video images and the current field of view of live 3D video images is less than the threshold.

When the result of the determination at block 1002 is "No", the position of the surgical tool and the positions of the surface of the anatomic structure in the FOV of the live 3D video images are tracked at block 1008. The method 1000 then includes determining whether the difference between the position of the surgical tool and the positions of the surface of the anatomic structure is less than a threshold distance at block 1010. Block 1010 may include determining the perpendicular distance between a position of a tip of the surgical tool and the surface of the anatomic structure. If the result of the determination at block 1010 is "Yes", a warning message that the surgical tool is approaching an anatomic structure is displayed on the display 102 at block 1012 and the method 1000 returns to block 1008. In aspects, that warning message may be displayed in the first window 110 illustrated in FIG. 1. In aspects, the functionality of blocks 1008, 1010, and 1012 may be made available for both manual VATS and RATS. In the case of RATS, all instrument motion may be limited by the robotic system when the user FOV and the endoscopic FOV do not match. If the result of the determination at block 1010 is "No", the method 1000 returns to block 1002.

In some cases, the clinician may change the FOV of the recorded 3D video images such that an anatomic structure of interest is occluded by another anatomic structure. For example, the clinician may change the FOV of the recorded 3D video images such that the FOV is on the backside of an anatomic structure of interest, but the anatomic structure of interest may be hidden by another anatomic structure. In some aspects, the clinician may change a setting or select a button to remove or make transparent or semitransparent the other anatomic structure so that the clinician can view the anatomic structure of interest.

Figure 11:
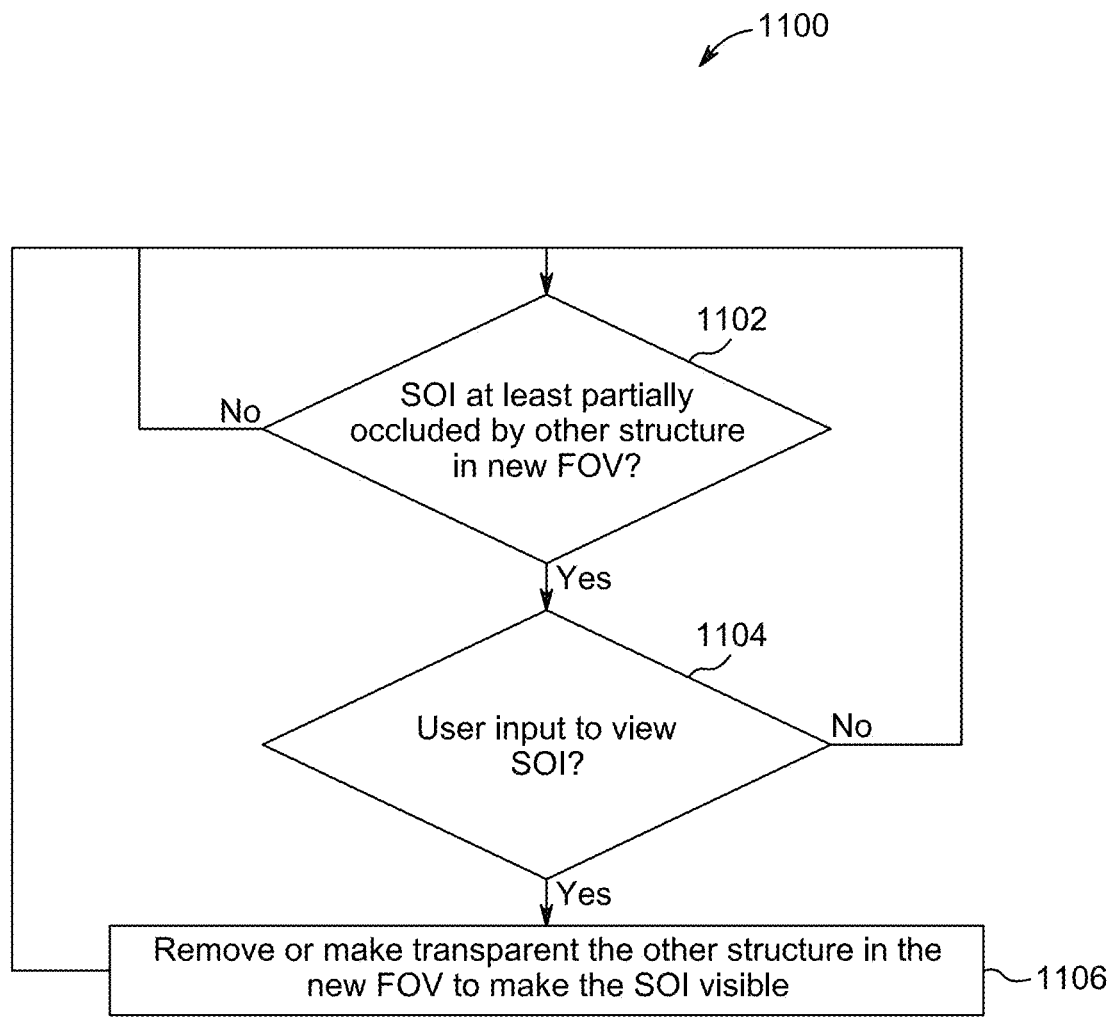

FIG. 11 illustrates an example method 1100 modifying an obstructing anatomic structure shown in a current FOV so that an anatomic structure of interest (SOI) hidden by the obstructing anatomic structure can be made visible. The method 1100 includes determining, at block 1102, whether a structure of interest is at least partially occluded by another structure shown in a new FOV moved to by a clinician. Block 1102 may include performing signal processing on the recorded 3D video images to recognize whether the anatomic SOI is no longer visible.

If the result of the determination at block 1102 is "Yes", the method 1100 includes determining whether there is user input to view the SOI at block 1104. The user input may be a user setting, e.g., a setting to view the SOI whenever the SOI is completely hidden by another anatomic structure. If the result of the determination at block 1104 is "Yes", the other structure in the new FOV is removed or made transparent or semitransparent to make the SOI visible at block 1106. Block 1106 may include aligning the new FOV with a 3D model and replacing the new FOV with a 3D model modified so that the other structure is removed from the 3D model. After block 1106 or if the determinations at blocks 1102 or 1104 are "No", the method 1100 returns to block 1102.

While the live video images are being displayed, the clinician may place marks at different locations on the live video images. In those aspects in which the clinician places marks on the live video images, the marks may be recorded on or in association with the recorded video images so that the clinician can later find and view those marked, recorded video images.

Figure 12:
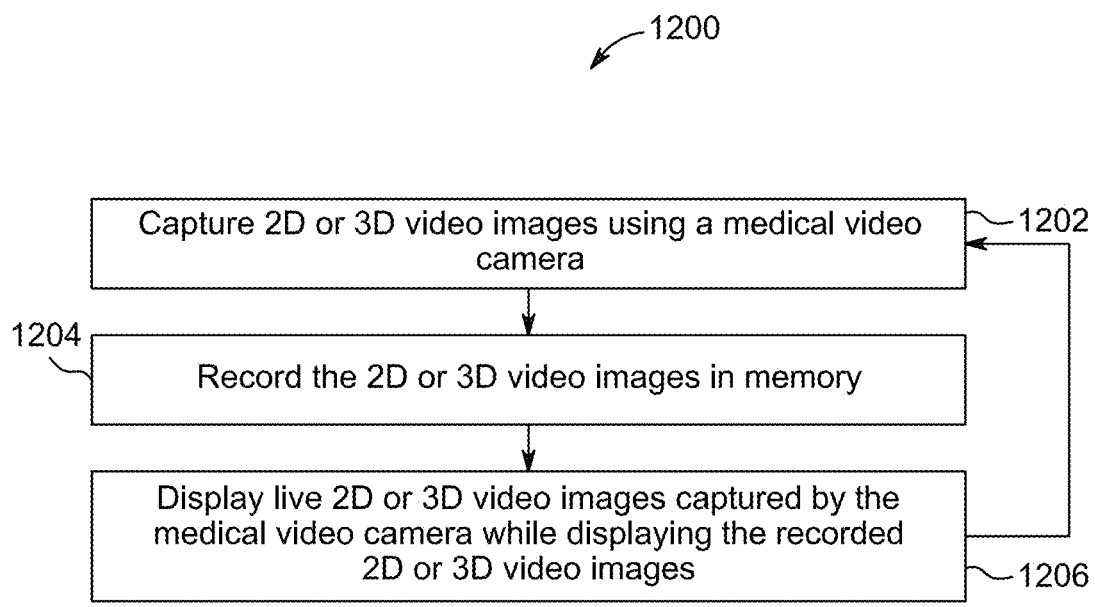

FIG. 12 is a flowchart of an example of a method of displaying live and recorded video images according to the disclosure. At block 1202, 2D or 3D video images are captured using a medical video camera, such as a laparoscopic camera, a 3D endoscopic camera, or any other suitable video camera for capturing 2D or 3D video images. Then, at block 1204, the 2D or 3D video images captured by the medical video camera are recorded in memory. In some aspects, the clinician may place marks on the live video images. Those marks may be recorded on or in association with the recorded video images so that the clinician can later find and view those marked, recorded video images when they are displayed at block 1206, e.g., by scrolling through the recorded video images. In aspects, all or a portion of the captured video images may be recorded based on user input. For example, the user may operate one or more suitable user controls, e.g., the user may use a cursor to toggle the record button 216 of FIG. 2, to record a range of live video images.

At block 1206, as 2D or 3D video images are being captured, they are displayed as live video images while the recorded video images are displayed. In some aspects, during normal operation only the live video images may be shown on the display 102. Then, the clinician may select a button or any other suitable user control to cause the recorded video images or the previously created 3D model to also be displayed. In some aspects, the user may be able to interact with these previously recorded video images or the 3D model. For example, FIGS. 6-11, illustrate different examples of user interactions with the previously recorded video images or the 3D model.

In aspects, as described herein, this disclosure features an intraoperative method. The intraoperative method includes capturing, by a 3D video camera, live 3D video images and recording the live 3D video images to obtain recorded 3D video images. The intraoperative method also includes simultaneously displaying the recorded 3D video images and the live 3D video images and displaying a 3D representation of an instrument overlaid on the live 3D video images. The intraoperative method further includes receiving movement commands from a remote computing device and moving the 3D representation of the instrument according to the received movement commands.

The intraoperative method may further include displaying movement through or change in orientation of the recorded 3D video images in response to a signal and adding a representation of an instrument or annotations to the recorded 3D video image in response to a signal. The intraoperative method may further include permanently adding or overlaying a 3D representation of the instrument or the annotations to the live video images in response to a signal to return to the live 3D video images.

In aspects, this disclosure features a system, which includes a processor and a memory having stored thereon instructions. The instructions, when executed by the processor, cause the processor to record at least a portion of a plurality of video images captured by a video camera to obtain a plurality of recorded video images. The instructions, when executed by the processor, also cause the processor to receive a signal highlighting an anatomic structure in one recorded video image of the plurality of recorded video images, and to detect and highlight the anatomic structure in the plurality of recorded video images. The instructions, when executed by the processor, also cause the processor to receive a signal to display at least one of the plurality of recorded video images with the highlighted anatomic structure and display the at least one of the plurality of recorded video images and a plurality of current video images captured by the video camera.

From the foregoing and with reference to the various figures, those skilled in the art will appreciate that certain modifications can be made to the disclosure without departing from the scope of the disclosure.

While detailed aspects are disclosed herein, the disclosed aspects are merely examples of the disclosure, which may be embodied in various forms and aspects. For example, aspects of an electromagnetic navigation system, which incorporates the target overlay systems and methods, are disclosed herein; however, the target overlay systems and methods may be applied to other navigation or tracking systems or methods known to those skilled in the art. Therefore, specific structural and functional details disclosed herein are not to be interpreted as limiting, but merely as a basis for the claims and as a representative basis for teaching one skilled in the art to variously employ the disclosure in virtually any appropriately detailed structure.

While several aspects of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of aspects. Those skilled in the art will envision other modifications within the scope and spirit of the claims appended hereto.

What is claimed is:

1. An intraoperative method comprising:
   capturing, by a video camera, video images;
   recording at least a portion of the video images, yielding recorded video images;
   causing simultaneous display of at least a portion of the recorded video images and current video images captured by the video camera;
   receiving a signal to highlight an anatomic structure;
   determining positions of the anatomic structure in the at least a portion of the recorded video images; and
   highlighting, in response to the signal to highlight the anatomic structure, the anatomic structure in the at least a portion of the recorded video images based on the positions of the anatomic structure, yielding a highlighted anatomic structure;
   determining that the highlighted anatomic structure is outside of a window; and
   in response to determining that the highlighted anatomic structure is outside of the window, causing display of an object in the window indicating a direction of a position of the highlighted anatomic structure or the direction, in the recorded video images, of a recorded video image that contains at least a portion of the highlighted anatomic structure.

2. The method of claim 1, wherein the video camera is a laparoscopic video camera or an endoscopic video camera.

3. The method of claim 1, further comprising receiving a signal indicating selection of at least one of the current video images,
   wherein recording the at least a portion of the video images includes recording the selected at least one of the current video images.

4. The method of claim 1, further comprising:
   causing display of the current video images in a first window; and
   causing display of the at least a portion of the recorded video images in a second window.

5. The method of claim 4, wherein the second window is smaller than the first window, and
   further comprising overlaying the second window on the first window.

6. The method of claim 5, further comprising overlaying the second window on a corner portion or a quadrant of the first window.

7. The method of claim 1, further comprising:
   causing display of the current video images in a first window; and
   causing display of the at least a portion of the recorded video images in a second window, which is smaller than the first window and which is overlaid on the first window.

8. The method of claim 1, further comprising causing display of the at least a portion of the recorded video images as semitransparent video images overlaid on the current video images.

9. The method of claim 1, further comprising causing display of forward or backward movement through the recorded video images in response to a signal to move through the recorded video images in a forwards or backwards direction, respectively, while causing display of the current video images.

10. A system comprising:
    a video capturing device configured to capture video images;
    a processor;
    a memory coupled to the processor and configured to store at least a portion of the video images, yielding stored video images; and
    a display configured to simultaneously display at least a portion of the stored video images and current video images captured by the video capturing device,
    wherein the memory is further configured to store instructions, which, when executed by the processor, causes the processor to:
    receive a signal to highlight an anatomic structure;
    determine a position of the anatomic structure in the at least a portion of the stored video images; and
    highlight, in response to the signal to highlight the anatomic structure, the anatomic structure in the at least a portion of the stored video images based on the positions of the anatomic structure, yielding a highlighted anatomic structure;
    cause display of a window on the display;
    determine that the highlighted anatomic structure is outside of the window; and
    in response to determining that the highlighted anatomic structure is outside of the window, cause display of an object in the window indicating a direction of a position of the highlighted anatomic structure or the direction, in the stored video images, of a stored video image that contains at least a portion of the highlighted anatomic structure.

11. The system of claim 10, wherein the video capturing device is a laparoscopic video camera or an endoscopic video camera.

12. The system of claim 10, wherein the instructions, when executed by the processor, further cause the processor to receive a user selection of at least one of the current video images, and
   wherein storing the at least a portion of the video images includes storing the user selection of the at least one of the current video images.

13. The system of claim 10, wherein the instructions, when executed by the processor, further cause the processor to:
   cause display of a first window and a second window on the display;
   cause display of the current video images in the first window; and
   cause display of the at least a portion of the stored video images in the second window.

14. The system of claim 13, wherein the second window is smaller than the first window, and
   wherein the instructions, when executed by the processor, further cause the processor to overlay the second window on the first window.

15. The system of claim 14, wherein the instructions, when executed by the processor, further cause the processor to overlay the second window on a corner portion or a quadrant of the first window.

16. The system of claim 10, wherein the instructions, when executed by the processor, further cause the processor to:
   receive a signal to move through the stored video images in a forwards or backwards direction; and
   cause display of forward or backward movement through the stored video images in response to the signal to move through the stored video images in a forwards or backwards direction, respectively, while causing display of the current video images.

17. The system of claim 10, wherein the instructions, when executed by the processor, further cause the processor to cause display of the at least a portion of the stored video images as semitransparent video images overlaid on the current video images.

18. A system comprising:
   a video capturing device configured to capture video images;
   a display configured to display the video images;
   a processor; and
   a memory configured to store the video images, yielding stored video images, and configured to store instructions, which, when executed by the processor, causes the processor to:
      cause simultaneous display of a first window and a second window on the display;
      cause display of current video images in the first window;
      cause display of the stored video images in the second window;
      receive a signal to move through the stored video images;
      cause display of movement through the stored video images in response to the signal to move through the stored video images;
      receive a signal to highlight an anatomic structure;
      determine a position of the anatomic structure in the stored video images;
      highlight, in response to the signal to highlight the anatomic structure, the anatomic structure in the stored video images based on the positions of the anatomic structure;
      determine that the highlighted anatomic structure is outside of the second window; and
      in response to determining that the highlighted anatomic structure is outside of the second window, cause display of an object in the second window indicating a direction of a position of the highlighted anatomic structure or the direction, in the stored video images, of a recorded video image that contains at least a portion of the highlighted anatomic structure.

* * * * *